(12) United States Patent
Sakuma et al.

(10) Patent No.: US 12,715,946 B2
(45) Date of Patent: Aug. 25, 2026

(54) COMPOSITION

(71) Applicants: JOSHO GAKUEN EDUCATIONAL FOUNDATION, Osaka (JP); ADEKA CORPORATION, Tokyo (JP)

(72) Inventors: Shinji Sakuma, Osaka (JP); Takumi Tomono, Osaka (JP); Kohei Miyata, Tokyo (JP); Koichi Shigeno, Tokyo (JP)

(73) Assignees: Josho Gakuen Educational Foundation, Osaka (JP); Adeka Corporation, Tokyo (JP)

( * ) Notice: Subject to any disclaimer, the term of this patent is extended or adjusted under 35 U.S.C. 154(b) by 531 days.

(21) Appl. No.: 18/248,565

(22) PCT Filed: Oct. 11, 2021

(86) PCT No.: PCT/JP2021/037523
§ 371 (c)(1),
(2) Date: Apr. 11, 2023

(87) PCT Pub. No.: WO2022/080294
PCT Pub. Date: Apr. 21, 2022

(65) Prior Publication Data

US 2023/0383037 A1 Nov. 30, 2023

(30) Foreign Application Priority Data

Oct. 16, 2020 (JP) ................................ 2020-174704

(51) Int. Cl.
*A61K 47/34* (2017.01)
*A61K 47/36* (2006.01)
*C08F 222/38* (2006.01)

(52) U.S. Cl.
CPC ........... *C08F 222/38* (2013.01); *A61K 47/34* (2013.01); *A61K 47/36* (2013.01)

(58) Field of Classification Search
CPC ........ C08F 222/38; A61K 47/34; A61K 47/36
See application file for complete search history.

(56) References Cited

U.S. PATENT DOCUMENTS

| | | | |
|---|---|---|---|
| 2012/0065124 | A1 | 3/2012 | Morishita et al. |
| 2018/0016366 | A1 | 1/2018 | Sakuma et al. |
| 2018/0044381 | A1 | 2/2018 | Sakuma et al. |
| 2019/0111141 | A1 | 4/2019 | Lee et al. |
| 2020/0071263 | A1 | 3/2020 | Bay et al. |
| 2021/0268113 | A1 | 9/2021 | Sakuma et al. |

FOREIGN PATENT DOCUMENTS

| | | | |
|---|---|---|---|
| JP | 2010502667 | A | 1/2010 |
| JP | 2010100781 | A | 5/2010 |
| JP | 2011229495 | A | 11/2011 |
| JP | 2019522020 | A | 8/2019 |
| WO | 2010134537 | A1 | 11/2010 |
| WO | 2016136707 | A1 | 9/2016 |
| WO | 2016136708 | A1 | 9/2016 |
| WO | 2020013265 | A1 | 1/2020 |

OTHER PUBLICATIONS

International Search Report and Written Opinion in International Application No. PCT/JP2021/037523, 14 pages, with partial translation. Dec. 7, 2021.

(Continued)

*Primary Examiner* — Sikarl A Witherspoon
(74) *Attorney, Agent, or Firm* — Heslin Rothenberg Farley & Mesiti P.C.

(57) ABSTRACT

The object of the present invention is to provide an absorption enhancer capable of introducing high-molecular weight compounds into cells.

The object can be solved by a composition of the present invention comprising a polymer compound having a group represented by the following general formula (1) or the following general formula (2) at a side chain, and a compound to be administered with a molecular weight of 1,000 to 1,200,000.

(1)

wherein $X^1$ is a residue of neutral amino acid or ω-aminoalkanoic acid in which an end amino group and an end carboxyl group are removed, $X^2$ is a residue of cell-penetrating peptide in which an end amino group and an end carboxyl group are removed, $X^3$ is a hydroxyl group, an amino group, an alkoxyl group having 1 to 4 carbon atoms or a benzyloxy group, a is an integer of 0 to 50, and * denotes a bonding site.

(2)

wherein $X^4$ is a residue of neutral amino acid or ω-aminoalkanoic acid in which an end amino group and an end carboxyl group are removed, $X^5$ is a residue of cell-penetrating peptide in which an end amino group and an end carboxyl group are removed, $X^6$ is a hydrogen atom, an alkyl group having 1 to 6 carbon atoms, a benzyl group, an acyl group having 1 to 6 carbon atoms, an arylsulfonyl group or an oxycarbonyl group, b is an integer of 0 to 50, and * denotes a bonding site.

6 Claims, 3 Drawing Sheets

Specification includes a Sequence Listing.

(56) References Cited

OTHER PUBLICATIONS

Sakuma et al., "Drug Delivery System", vol. 28, pp. 109-118, with abstract. 2013.
Tabaru et al., "Enhancement of Nasal Absorption of Antibody Drug Using Cell-Penetrating Peptide-Linked Hyaluronic Acid", p. 170. Japanese Language Document. May 8, 2020.
Extended European Search Report in European Application No. 21880033.2, 11 pages. Feb. 4, 2025.
Mohri et al., "Potential of D-Octaarginine-Linked Polymers as an in Vitro Transfection Tool for Biomolecules", ACS Publications, Bioconjugate Chemistry, vol. 26, pp. 1782-1790. Aug. 2015.
Sakuma et al., "Cross-Reactivity of Immunoglobulin A Secreted on the Nasal Mucosa in Mice Nasally Inoculated with Inactivated H1N1 Influenza A Viruses in the Presence of D-Octaarginine-Linked Polymers", European Journal of Pharmaceutics and Biopharmaceutics, vol. 92, pp. 56-64. Feb. 2015.
Sakuma et al., "Oligoarginine-Linked Polymers as a New Class of Penetration Enhancers", Journal of Controlled Release, vol. 148, pp. 187-196. Aug. 2010.
Sakuma et al., "Performance of Cell-Penetrating Peptide-Linked Polymers Physically Mixed with Poorly Membrane- Permeable Molecules on Cell Membranes", European Journal of Pharmaceutics and Biopharmaceutics, vol. 81, pp. 64-73. Jan. 2012.
Ukawa et al., "Biodegradable Hyaluronic Acid Modified with Tetraglycine-L-Octaarginine as a Safe Adjuvant for Mucosal Vaccination", Molecular Pharmaceutics, vol. 16, pp. 1105-1118. Feb. 2019.
Jilin et al., "Experimental Guide to Medical Molecular Biology", China Medical Science and Technology Press, ISDBN 7-5067-3231-9, 7 pages with translation. Aug. 2005.

[Figure 1]
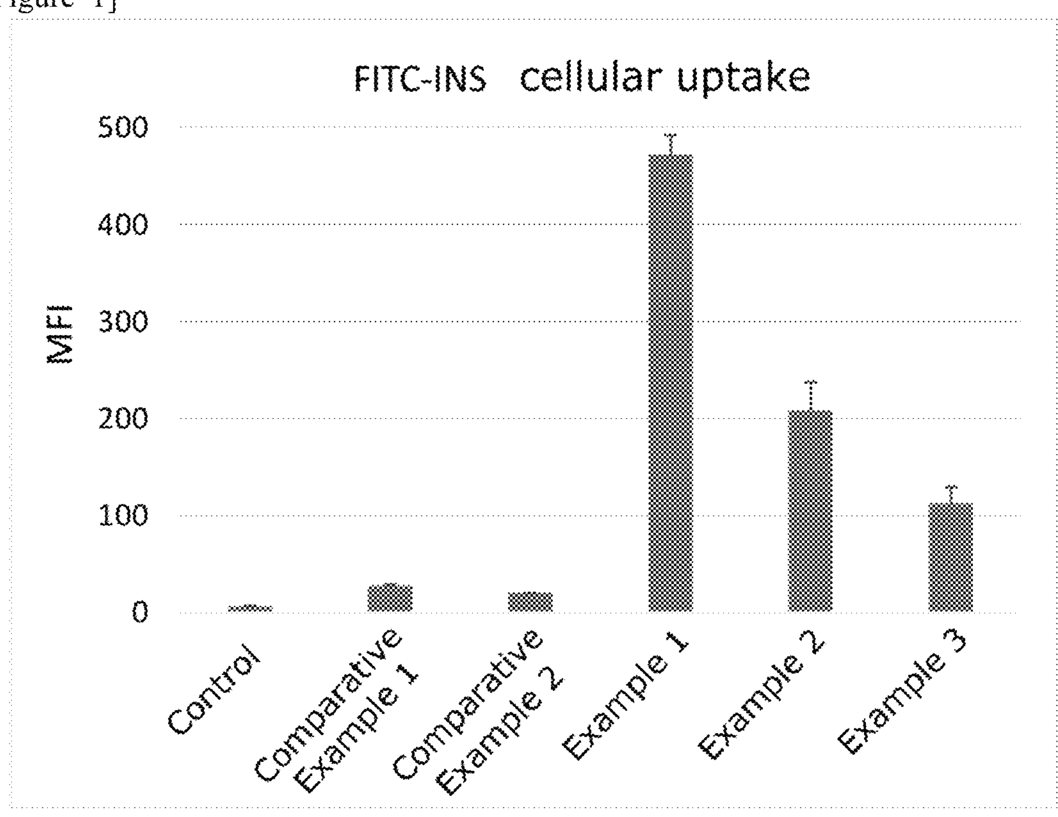
[Figure 2]
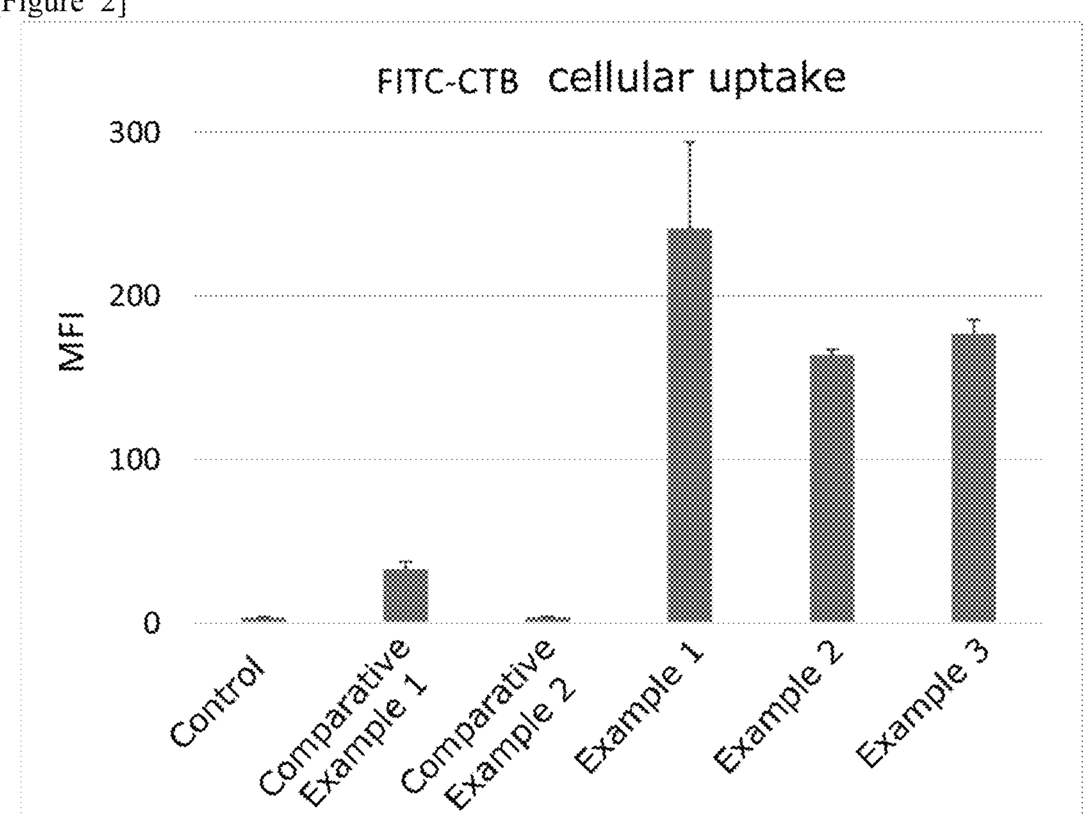

[Figure 3]
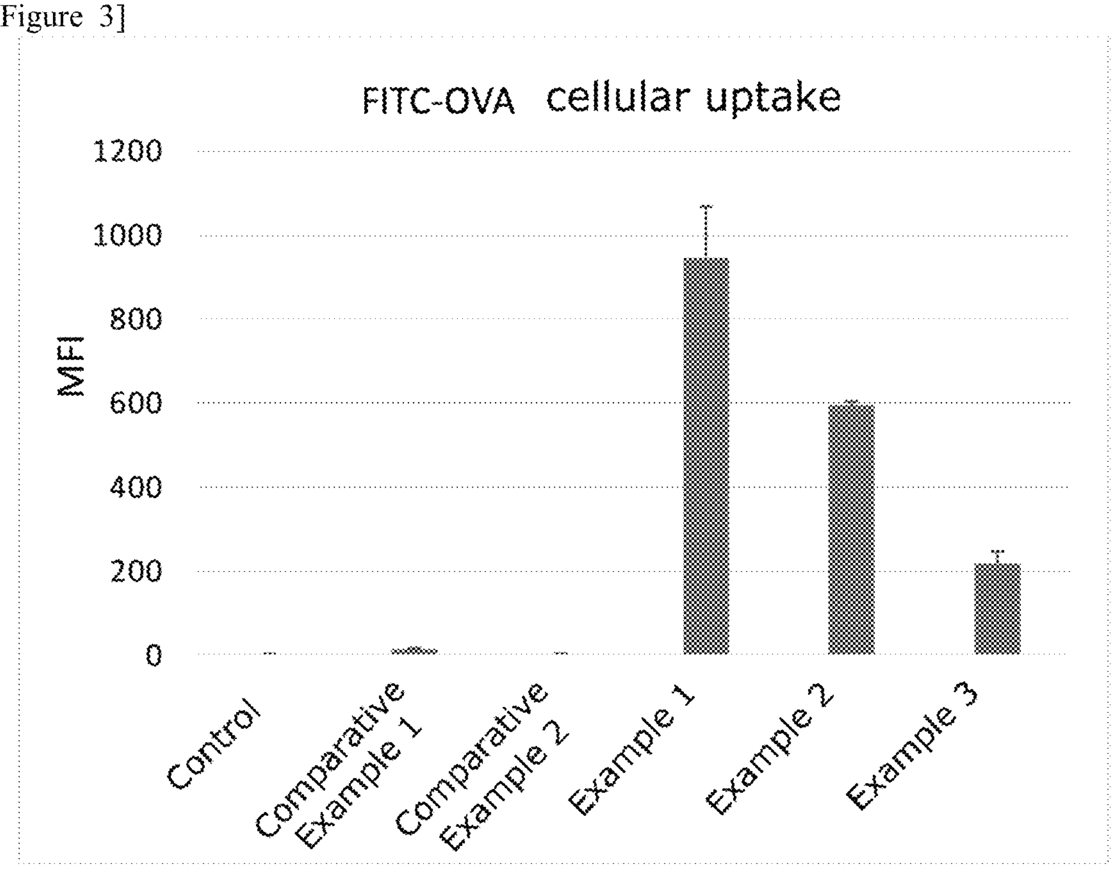
[Figure 4]
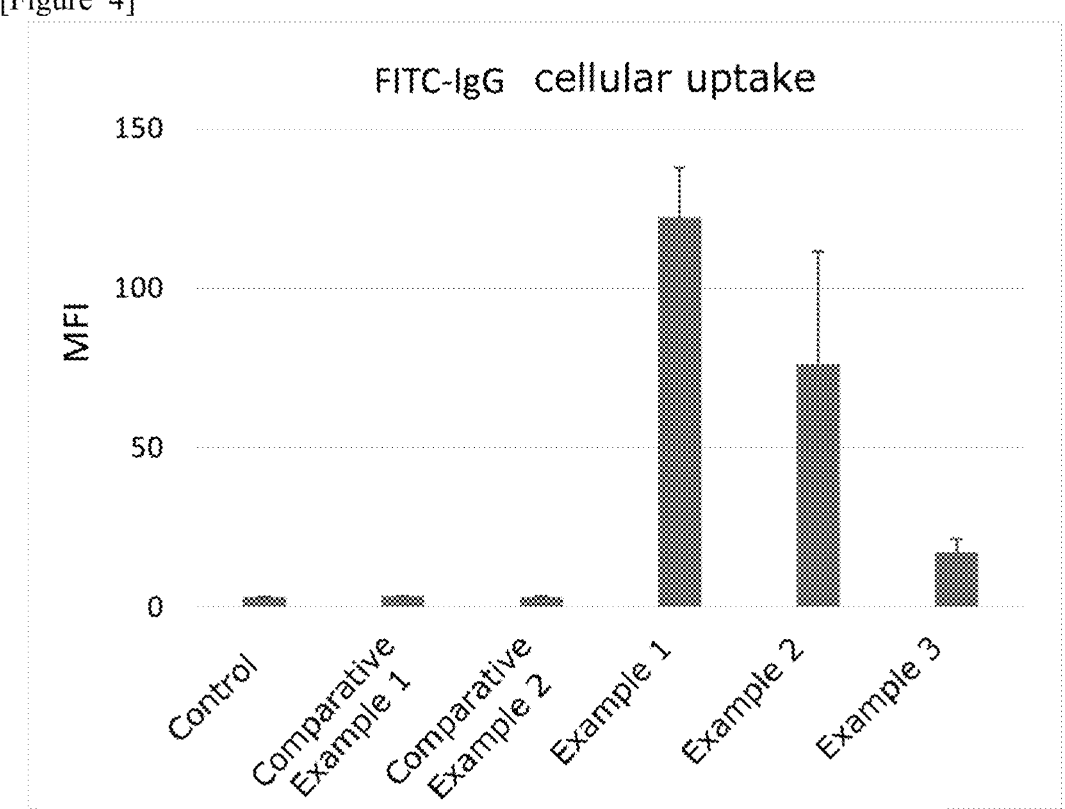

[Figure 5]
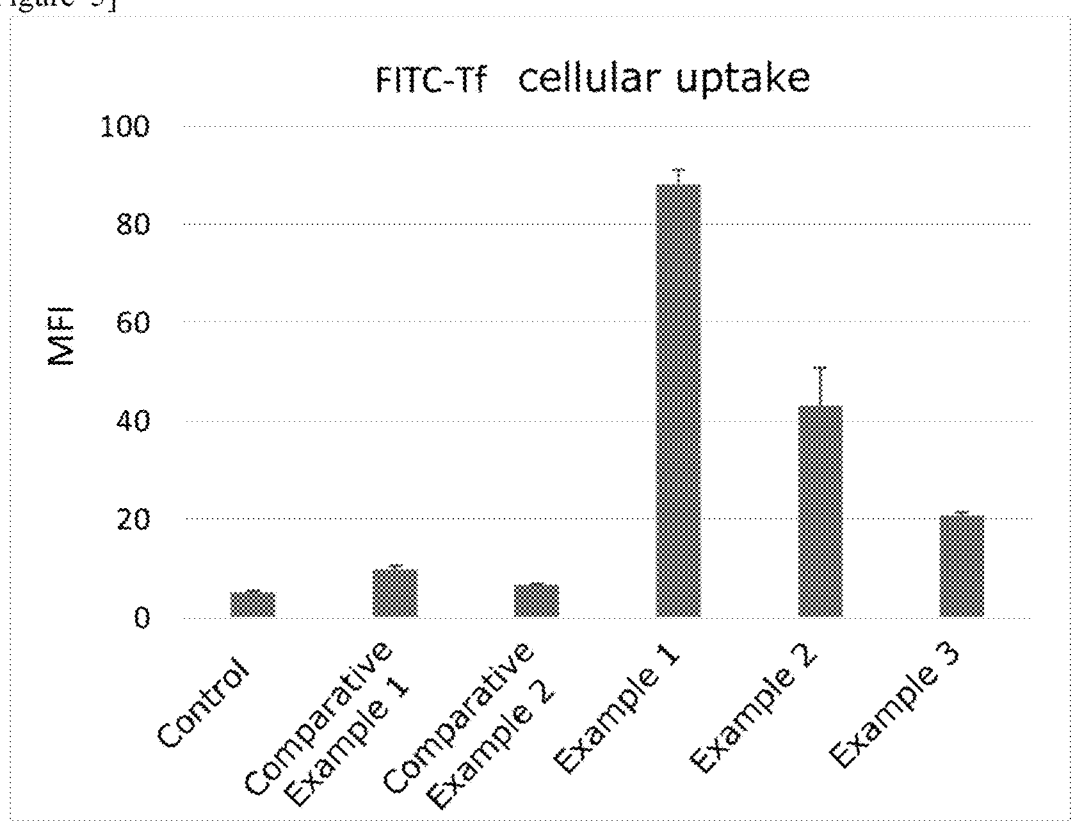
[Figure 6]
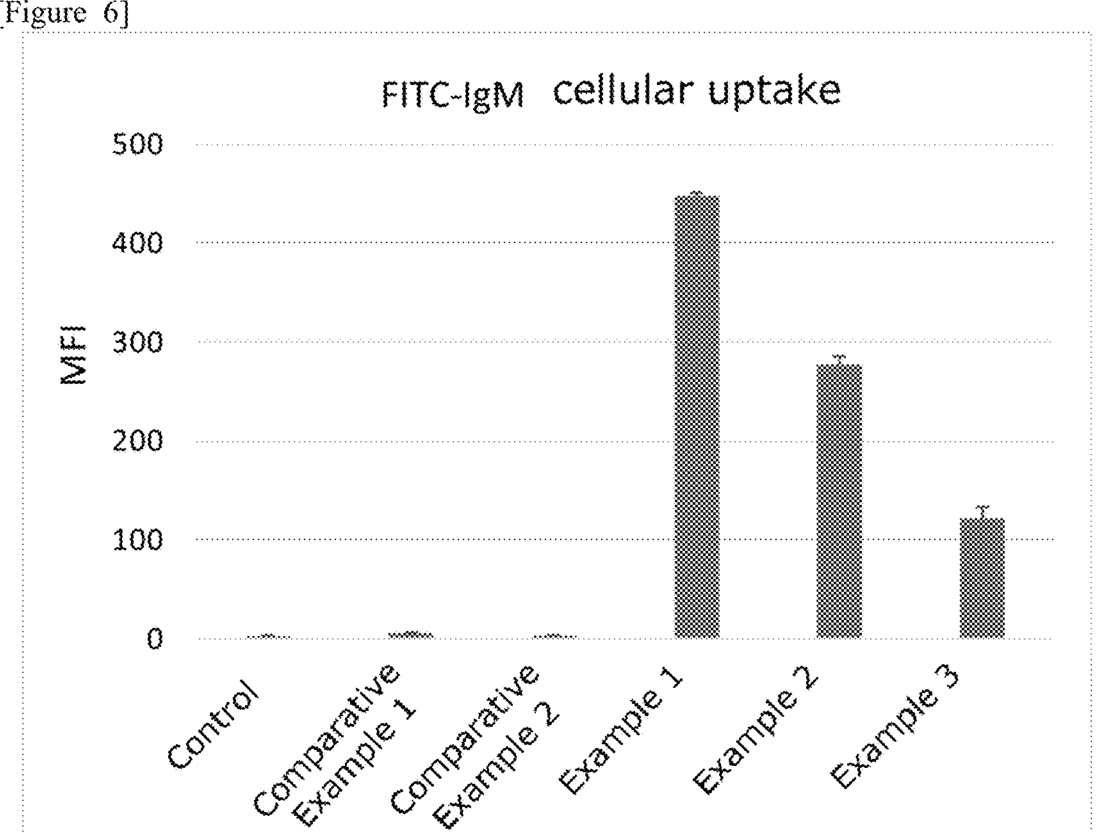

SEQUENCE LISTING

```
<160> NUMBER OF SEQ ID NOS: 12

<210> SEQ ID NO 1
<211> LENGTH: 13
<212> TYPE: PRT
<213> ORGANISM: Human immunodeficiency virus type 1

<400> SEQUENCE: 1

Gly Arg Lys Lys Arg Arg Gln Arg Arg Arg Pro Pro Gln
1               5                   10


<210> SEQ ID NO 2
<211> LENGTH: 17
<212> TYPE: PRT
<213> ORGANISM: Human immunodeficiency virus type 1

<400> SEQUENCE: 2

Thr Arg Gln Ala Arg Arg Asn Arg Arg Arg Arg Trp Arg Glu Arg Gln
1               5                   10                  15

Arg


<210> SEQ ID NO 3
<211> LENGTH: 15
<212> TYPE: PRT
<213> ORGANISM: Feline herpesvirus 1

<400> SEQUENCE: 3

Arg Arg Arg Arg Asn Arg Thr Arg Arg Asn Arg Arg Arg Val Arg
1               5                   10                  15


<210> SEQ ID NO 4
<211> LENGTH: 13
<212> TYPE: PRT
```

<213> ORGANISM: Human T-cell lymphotropic virus type 2

<400> SEQUENCE: 4

Thr Arg Arg Gln Arg Thr Arg Arg Ala Arg Arg Asn Arg
1 5 10

<210> SEQ ID NO 5
<211> LENGTH: 19
<212> TYPE: PRT
<213> ORGANISM: Canaine cytomegalovirus

<400> SEQUENCE: 5

Lys Leu Thr Arg Ala Gln Arg Arg Ala Ala Ala Arg Lys Asn Lys Arg
1 5 10 15

Asn Thr Arg

<210> SEQ ID NO 6
<211> LENGTH: 16
<212> TYPE: PRT
<213> ORGANISM: Artificial Sequence
<220> FEATURE:
<223> OTHER INFORMATION: Amphiphilic basic peptid

<400> SEQUENCE: 6

Arg Gln Ile Lys Ile Trp Phe Gln Asn Arg Arg Met Lys Trp Lys Lys
1 5 10 15

<210> SEQ ID NO 7
<211> LENGTH: 19
<212> TYPE: PRT
<213> ORGANISM: Artificial Sequence
<220> FEATURE:
<223> OTHER INFORMATION: Amphiphilic basic peptide

<400> SEQUENCE: 7

Lys Met Thr Arg Ala Gln Arg Arg Ala Ala Ala Arg Arg Asn Arg Trp
1 5 10 15

Thr Ala Arg

<210> SEQ ID NO 8
<211> LENGTH: 16
<212> TYPE: PRT
<213> ORGANISM: Artificial Sequence
<220> FEATURE:
<223> OTHER INFORMATION: Amphiphilic basic peptide

<400> SEQUENCE: 8

Arg Gln Ile Lys Ile Trp Phe Gln Asn Arg Arg Met Lys Trp Lys Lys
1 5 10 15

<210> SEQ ID NO 9
<211> LENGTH: 17
<212> TYPE: PRT
<213> ORGANISM: Artificial Sequence
<220> FEATURE:
<223> OTHER INFORMATION: Amphiphilic basic peptide

<400> SEQUENCE: 9

Asn Ala Lys Thr Arg Arg His Glu Arg Arg Arg Lys Leu Ala Ile Glu
1 5 10 15

Arg

<210> SEQ ID NO 10
<211> LENGTH: 34

-continued

```
<212> TYPE: PRT
<213> ORGANISM: Artificial Sequence
<220> FEATURE:
<223> OTHER INFORMATION: Amphiphilic basic peptide

<400> SEQUENCE: 10

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Asp Asp Pro
            20                  25                  30

Val Asp


<210> SEQ ID NO 11
<211> LENGTH: 27
<212> TYPE: PRT
<213> ORGANISM: Artificial Sequence
<220> FEATURE:
<223> OTHER INFORMATION: Hydrophobic basic peptide

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25


<210> SEQ ID NO 12
<211> LENGTH: 21
<212> TYPE: PRT
<213> ORGANISM: Artificial Sequence
<220> FEATURE:
<223> OTHER INFORMATION: Hydrophobic basic peptide

<400> SEQUENCE: 12

Ala Gly Tyr Leu Leu Gly Lys Ile Asn Leu Lys Ala Leu Ala Ala Leu
1               5                   10                  15

Ala Lys Lys Ile Leu
            20
```

COMPOSITION

CROSS REFERENCE TO RELATED APPLICATIONS

This application is a U.S. National Phase filing under 35 U.S.C. § 371 of International Application PCT/JP2021/037523, filed Oct. 11, 2021, and published as WO 2022/080294 A1 on Apr. 21, 2022.PCT/JP2021/037523 claims priority from Japanese application number 2020-174704, filed Oct. 16, 2020. The entire contents of each of these prior applications are hereby incorporated herein by reference.

SEQUENCE LISTING

The instant application contains an electronic sequence listing. The contents of the electronic sequence listing (ASCII; H2671819.txt; Size: 3,481 bytes; and Date of Creation: May 12, 2023) is herein incorporated by reference in its entirety.

TECHNICAL FIELD

The present invention relates to a composition. According to the present invention, high molecular weight compounds such as antibody drugs can be introduced into cells.

BACKGROUND ART

For example, salcaprozate sodium (SNAC: N-(8-[2-hydroxybenzoyl]amino)caprylic acid) is known as an absorption enhancer for medicines and the like (Patent literature 1). SNAC is administered in coexistence with medicines and the like, but it has been difficult to introduce high-molecular-weight compounds into cells.

In addition, there are methods in which cell-penetrating peptides are used as absorption enhancers. For example, a method in which cell-penetrating peptides are coexistent with a target compound to be introduced into cells and only the target compound is introduced (Patents literatures 2 and 3) is known. The method using cell-penetrating peptides is simple, but the efficiency of introduction of high molecular weight substances is not sufficient.

CITATION LIST

Patent Literature

[Patent literature 1] JP 2010-502667 A
[Patent literature 2] WO 2010/134537
[Patent literature 3] JP 2019-522020 A
[Patent literature 4] WO 2016/136708

SUMMARY OF INVENTION

Technical Problem

The present inventors found that the introduction of low-cell-penetrating compounds into cells was promoted by using a polymer compound with a cell-penetrating peptide attached to the side chain of the polymer compound (Patent literature 4). However, it has been expected to develop an absorption enhancer capable of introducing high-molecular weight compounds into cells.

The object of the present invention is to provide an absorption enhancer capable of introducing high-molecular weight compounds into cells.

Solution to Problem

The present inventors have conducted intensive studies into an absorption enhancer capable of introducing high-molecular weight compounds into cells, and as a result, surprisingly found that by combining a high-molecular-weight compound with a peptide of a specific structure in the side chain, it is possible to efficiently introduce a high-molecular-weight compound into the cells.

The present invention is based on the above findings.

Accordingly, the present invention relates to:

[1] a composition comprising a polymer compound having a group represented by the following general formula (1) or the following general formula (2) at a side chain, and a compound to be administered with a molecular weight of 1,000 to 1,200,000.

(1)

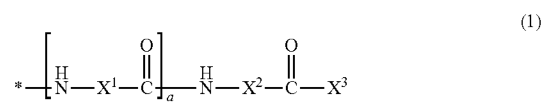

wherein $X^1$ is a residue of neutral amino acid or ω-aminoalkanoic acid in which an end amino group and an end carboxyl group are removed, $X^2$ is a residue of cell-penetrating peptide in which an end amino group and an end carboxyl group are removed, $X^3$ is a hydroxyl group, an amino group, an alkoxyl group having 1 to 4 carbon atoms or a benzyloxy group, a is an integer of 0 to 50, and * denotes a bonding site.

(2)

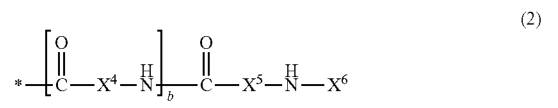

wherein $X^4$ is a residue of neutral amino acid or ω-aminoalkanoic acid in which an end amino group and an end carboxyl group are removed, $X^5$ is a residue of cell-penetrating peptide in which an end amino group and an end carboxyl group are removed, $X^6$ is a hydrogen atom, an alkyl group having 1 to 6 carbon atoms, a benzyl group, an acyl group having 1 to 6 carbon atoms, an arylsulfonyl group or an oxycarbonyl group, b is an integer of 0 to 50, and * denotes a bonding site,

[2] the composition of the item [1], wherein the molecular weight of the compound to be administered is 1,000 to 200,000,

[3] the composition of the item [1] or [2], wherein a main chain polymer of the polymer compound is a vinyl hydrophilic polymer,

[4] the composition of any one of the items [1] to [3], wherein the compound to be administered is an antibody,

[5] the composition of the item [4], wherein the antibody is a polyclonal antibody, monoclonal antibody, chimeric antibody, humanized antibody, or human antibody, or antigen-binding fragment thereof, and

[6] the composition of any one of the items [1] to [5], for contacting cells after mixing the polymer compound and the compound to be administered.

Advantageous Effects of Invention

According to the composition of the present invention, it is possible to introduce high molecular weight compounds into cells. In particular, it is possible to enhance the absorption of drugs such as antibody drugs in vivo, and to improve the efficacy of drugs.

BRIEF DESCRIPTION OF THE DRAWINGS

FIG. 1 The graph shows the cellular uptake of the composition of the present invention with FITC-INS as the compound to be administered.

FIG. 2 The graph shows the cellular uptake of the composition of the present invention with FITC-CTB as the compound to be administered.

FIG. 3 The graph shows the cellular uptake of the composition of the present invention with FITC-OVA as the compound to be administered.

FIG. 4 The graph shows the cellular uptake of the composition of the present invention with FITC-IgG as the compound to be administered.

FIG. 5 The graph shows the cellular uptake of the composition of the present invention with FITC-Tf as the compound to be administered.

FIG. 6 The graph shows the cellular uptake of the composition of the present invention with FITC-IgM as the compound to be administered.

DESCRIPTION OF EMBODIMENTS

The composition of the present invention comprises a polymer compound having a group represented by the following general formula (1) or the following general formula (2) at a side chain, and a compound to be administered with a molecular weight of 1,000 to 1,200,000.

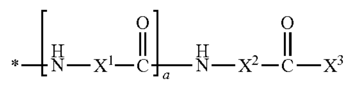

(1)

wherein $X^1$ is a residue of neutral amino acid or ω-aminoalkanoic acid in which an end amino group and an end carboxyl group are removed, $X^2$ is a residue of cell-penetrating peptide in which an end amino group and an end carboxyl group are removed, $X^3$ is a hydroxyl group, an amino group, an alkoxyl group having 1 to 4 carbon atoms or a benzyloxy group, a is an integer of 0 to 50, and * denotes a bonding site.

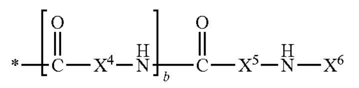

(2)

wherein $X^4$ is a residue of neutral amino acid or ω-aminoalkanoic acid in which an end amino group and an end carboxyl group are removed, $X^5$ is a residue of cell-penetrating peptide in which an end amino group and an end carboxyl group are removed, $X^6$ is a hydrogen atom, an alkyl group having 1 to 6 carbon atoms, a benzyl group, an acyl group having 1 to 6 carbon atoms, an arylsulfonyl group or an oxycarbonyl group, b is an integer of 0 to 50, and * denotes a bonding site. The molecular weight of the compound to be administered may be, for example, 1,000~200,000

The composition of the present invention comprises the polymeric compound and the compound to be administered, and can efficiently introduce the compound to be administered into cells. Therefore, the composition of the present invention is not limited, but is a composition for introducing a compound. In addition, when the compound to be administered is a drug and is used for treating humans, animals, or the like, the composition of the present invention can be used as a pharmaceutical composition. For example, the composition of the present invention can be introduced the compound into cells through mucous membranes (such as, nasal mucosa, oral mucosa, vaginal mucosa, rectal mucosa, eye mucosa, gastric mucosa, intestinal mucosa, or the like).

<<Compound to be Administered>>

The composition of the present invention can introduce high molecular weight compound to be administered into cells as shown in the examples. The molecular weight of the compound to be administered is not particularly limited, but from the viewpoint of exhibiting the effect of the present invention remarkably, the molecular weight is, for example, 1,000 to 1,200,000, in an embodiment, 4,000 to 1,100,000, in an embodiment, 4,000 to 1,100,000, in an embodiment, 5,000 to 1,000,000, in an embodiment, 9,000 to 990,000, in an embodiment, 20,000 to 980,000, in an embodiment, 40,000 to 950,000, in an embodiment, 70,000 to 940,000, in an embodiment, 85,000 to 930,000, in an embodiment, 100,000 to 920,000, in an embodiment, 130,000 to 910,000, in an embodiment, 140,000 to 905,000, in an embodiment, 150,000 to 900,000, in an embodiment, 160,000 to 890,000, in an embodiment, 170,000 to 880,000, in an embodiment, 180,000 to 870,000, in an embodiment, 190,000 to 860,000, in an embodiment, 200,000 to 850,000, in an embodiment, 230,000 to 830,000, in an embodiment, 250,000 to 800,000, in an embodiment, 300,000 to 750,000, in an embodiment, 350,000 to 700,000, in an embodiment, 400,000 to 650,000, in an embodiment, 450,000 to 600,000, in an embodiment, 500,000 to 550,000. In addition, the molecular weight is, in an embodiment, 1,000 to 200,000, in an embodiment, 5,000 to 200,000, in an embodiment, 20,000 to 180,000, in an embodiment, 40,000 to 180,000, in an embodiment, 70,000 to 170,000, in an embodiment, 85,000 to 160,000, in an embodiment, 100,000 to 155,000. The upper limits and lower limits of the above molecular weight range can be combined as appropriate, for example, 1,000 to 1,100,000, 4,000 to 1,200,000, or the like.

The molecular weight of the compound to be administered is the ratio of the mass of one molecule of the substance to the unified atomic mass unit, which means the sum of the atomic mass contained in the molecule. Therefore, it can be calculated from the chemical formula of each compound. Unless otherwise specified, the relative atomic masses (atomic weights) based on the natural nuclide compositions of the constituent elements are used in the calculation. If the compound to be administered is a mixture, it can be calculated from the ratio of two or more mixed compounds.

If the compound to be administered is a polymer, or a mixture with an unknown mixing ratio, the weight average molecular weight can be used as the molecular weight. In this specification, the term "weight average molecular weight" means the weight average molecular weight in the case of GPC analysis using aqueous solvents. For example, the weight average molecular weight in terms of pullulan, or the weight average molecular weight in terms of polyethylene glycol (PEG) or polyethylene oxide (PEO) can be used.

If the compound to be administered is an antibody, protein, or the like, the weight average molecular weight converted to Thyroglobulin, γ-Globulin, BSA, OVA, Myoglobin, Ribonuclease A, Aprotinin equivalent, for example, can be used in addition to the above conversion. When the compound to be administered is an antibody, protein, or the like, the molecular weight in GPC measurement is not limited, but, for example, the values measured by the following apparatus and columns, can be used Instrument: EXTREMA(JASCO Corporation)

Column: PROTEIN LW-803(Shodex)

The compound to be administered is not limited, but includes biopharmaceuticals such as antibodies, drugs such as a peptide/protein drug such as an insulin, and an insulin secretion promoter (e.g., exendin-4 and GLP-1), a steroid hormone, a non-steroidal analgesic anti-inflammatory drug, a tranquilizer, an anti-hypertensive drug, a therapeutic drug for an ischemic heart disease, an anti-histamine drug, an anti-asthmatic drug, an anti-parkinson drug, a cerebral circulation improving drug, an anti-emetic drug, an anti-depressant drug, an anti-arrhythmic drug, an anti-coagulant drug, an anti-gout drug, an anti-fungal drug, an anti-dementia drug, a therapeutic drug for Sjögren's syndrome, a narcotic analgesic drug, a beta blocker, a β1 agonist, a β2 agonist, a parasympathomimetic drug, an anti-tumor drug, a diuretic drug, an anti-thrombotic drug, a histamine H1 receptor antagonist, a histamine H2 receptor antagonist, an anti-allergic drug, a smoking cessation drug, and a vitamin; nucleic acid compounds such as a deoxyribonucleic acid (DNA), a ribonucleic acid (RNA), and analogs or derivatives thereof (e.g., a peptide nucleic acid (PNA) and a phosphorothioate DNA); peptide compounds such as an enzyme, a glycoprotein, and a transcription factor; and polysaccharide derivatives such as pullulan, amylopectin, amylose, glycogen, cyclodextrin, dextran, hydroxyethyldextran, mannan, cellulose, starch, alginic acid, chitin, chitosan, and hyaluronic acid, and derivatives thereof.

From the viewpoint of exhibiting the effect of the present invention remarkably, the compound to be administered is preferably biopharmaceuticals such as antibodies, peptide/protein drug such as an insulin, and an insulin secretion promoter (e.g., exendin-4 and GLP-1), nucleic acid compounds such as a deoxyribonucleic acid (DNA), a ribonucleic acid (RNA), and analogs or derivatives thereof (e.g., a peptide nucleic acid (PNA) and a phosphorothioate DNA), peptide compounds such as an enzyme, a glycoprotein, and a transcription factor, and further preferably antibodies, proteins, peptides or the like. FITC-BSA can be excluded from the compounds to be administered used in the present invention.

(Antibody)

The antibody includes, but is not limited to, a polyclonal antibody, monoclonal antibody, chimeric antibody, humanized antibody, or human antibody, or antigen-binding fragment thereof. The humanized antibodies are human immunoglobulins in which residues of the hypervariable region are substituted with residues of the hypervariable region of a non-human species (donor antibody) possessing the desired specificity, affinity and ability, such as mouse, rat, rabbit or non-human primate. The human antibodies are molecules derived from human immunoglobulins, and means that all amino acid sequences constituting the antibody, including the complementarity-determining region and the structural region, are entirely composed of the amino acid sequences of human immunoglobulins. The human antibodies can be produced by human beings, or by using a variety of techniques, including phage display libraries and other techniques disclosed in the this field. Further, The human antibodies can also be produced by administering antigens to transgenic animals that have been modified to produce antibodies in response to test inoculations of antigen, but whose endogenous locus is dysfunctional, such as immuno-treated xenomouse.

The antigen-binding fragments include Fab, Fab', F(ab')2, and Fv fragments, or single chain antibody molecules (scFv). Furthermore, diabody, triabody, tetrabody, domain antibody, minibody, scAb (single chain antibody), or multi-specific antibodies formed from the above antibody fragments can be used as antigen-binding fragments. These antigen-binding fragments can be obtained, for example, by digestion of antibodies with proteolytic enzymes (e.g., pepsin or papain) followed by purification by conventional methods of protein isolation and purification, or by genetic recombination. For example, the scFv (single-chain variable fragment) is a single-chain polypeptide antibody obtained by linking the heavy-chain variable domain (VH) and the light-chain variable domain (VL) with a linker. The order of the linkage between VH and VL is not particularly limited and they can be arranged in any order. That is, they may be arranged in the order of [VH]-linker-[VL], or in the order o [VH]-linker-[VL].

The above antibodies or antigen-binding fragments can be used as antibody drugs. Specific antibody drugs include bevacizumab, rituximab, trastuzumab, panitumumab, cetuximab, pertuzumab, trastuzumab-emtansine, brentuximab vedotin, trastuzumab, mepolizumab, gemtuzumab ozogamicin, mogamulizumab, alemtuzumab, inotuzumab, ofatumumab, ipilimumab, ramucirumab, nivolumab, or the like.

The content of the compounds to be administered in the composition of the present invention is not particularly limited, but from the viewpoint of exhibiting the effect of the present invention, preferably 0.00001~40% by weight, more preferably 0.0001~30% by weight, and most preferably 0.0001~20% by weight.

Polymer Compound

The polymer compound is a graft-type polymer compound having a group represented by the general formula (1) or the general formula (2) at a side chain (Group of General Formula (1))

In the general formula (1), $X^1$ represents a residue of a neutral amino acid or ω-aminoalkanoic acid in which an end amino group and an end carboxyl group are removed, and "a" is an integer of 0 to 50. The neutral amino acids include, for example, alanine, asparagine, cysteine, glutamine, glycine, isoleucine, leucine, methionine, phenylalanine, proline, serine, threonine, tryptophan, tyrosine, valine, hydroxyproline, or the like. The ω-aminoalkanoic acids include 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, 11-aminoundecanoic acid, or the like. The neutral amino acids applied to $X^1$ are preferably glycine, alanine, valine, isoleucine, leucine, serine, threonine, or phenylalanine, and more preferably glycine, alanine, or serine, most preferably glycine, since the introduction efficiency of the compound to be administered increases. From the viewpoint of exhibiting the effect of the present invention, the number of "a" is preferably 0 to 30, more preferably 0 to 20, most preferably 0 to 10. In an embodiment, a is 0, and in an embodiment, a is 4.

In the general formula (1), $X^2$ represents a residue of a cell-penetrating peptide in which an end amino group and an end carboxyl group are removed. The cell-penetrating peptide residue of the polymer compound in the present invention may be selected according to the compound to be administered which is introduced, the cell, and the mucous membrane.

From the viewpoint of exhibiting the effect of the present invention, it is preferable that at least one of the amino acids constituting the cell-penetrating peptide residue is a basic amino acid. Further, the basic amino acid can be either L-amino acid or D-amino acid, but preferably D-amino acid. Since D-amino acids are not usually present in the body, they are less likely to be degraded, and there is a possibility that the effect of the composition of the present invention is maintained.

The basic amino acids include arginine, ornithine, lysine, hydroxylysine, histidine, or the like. Among them, amino acids containing guanidino groups are preferable, and arginine is more preferable. The higher the ratio of basic amino acids in cell-penetrating peptide residues, the higher the efficiency of introduction of the compound to be administered. Therefore, the ratio of basic amino acids with respect to total amino acids constituting the cell-penetrating peptide is preferably 50% or more, and more preferably 70% or more, on a molar basis. In the amino acids constituting the cell-penetrating peptide residues, amino acids other than basic amino acids are preferably neutral amino acids.

In the present specification, the term "amino acid" means an $\alpha$-amino acid unless otherwise specified.

The number of amino acids constituting cell-penetrating peptide residues is preferably 5 to more preferably 6 to 20, and most preferably 7 to 15, since the introduction efficiency of the compound to be administered increases.

As the preferable examples of cell-penetrating peptides, there may be mentioned, an arginine oligomer in which 7 to 30 arginine are bonded by peptide bond, hydrophilic basic peptides such as a peptide with the amino acid sequence GRKKRRQRRRPPQ (commonly known as HIV-1 Tat: SEQ ID No:1), a peptide with the amino acid sequence TRQARRNRRRRWRERQR (commonly known as HIV-1 Rev: SEQ ID No:2), a peptide with the amino acid sequence RRRRNRTRRNRRRVR (commonly known as FHV Coat: SEQ ID No:3), a peptide with the amino acid sequence TRRQRTRRARRNR (commonly known as HTLV-II Rex: SEQ ID No:4), or a peptide with the amino acid sequence KLTRAQRRAAARKNKRNTR (CCMV Gag: SEQ ID No:5); amphiphilic basic peptides such as a peptide with the amino acid sequence RQIKIWFQNRRMKWKK (commonly known as antennapedia: SEQ ID No:6), a peptide with the amino acid sequence KMTRAQRRAAARRNRWTAR (commonly known as BMW Gag: SEQ ID No:7), a peptide with the amino acid sequence RQIKIWFQNRRMKWKK (commonly known as penetratin: SEQ ID No:8), a peptide with the amino acid sequence NAKTRRHERRRKLAIER (commonly c known as P22N: SEQ ID No: 9), a peptide with the amino acid sequence DAATATRGRSAASRPTERPRAPARSASRPDDPVD (commonly known as VP22: SEQ ID No: 10); hydrophobic basic peptides such as a peptide with the amino acid sequence GWTLNSAGYLLGKINLKALAALAKKIL (commonly known as transportan: SEQ ID No: 11), a peptide with the amino acid sequence AGYLLGKINLKALAALAKKIL (commonly known as TP-1:SEQ ID No: 12). Among these peptides, hydrophilic basic peptides are preferable because of their high introduction efficiency of the compound to be administered, and the arginine oligomer is further preferable. In the arginine oligomers, the number of repeats of arginine is preferably 7 to 20, more preferably 7 to 15, and most preferably 7 to 10, from the viewpoint of exhibiting the effect of the present invention. In an embodiment, the number of arginine repeats is 8.

In the general formula (1), $X^3$ represents a hydroxyl group, an amino group, an alkoxyl group having 1 to 4 carbon atoms or a benzyloxy group. The alkoxyl group having 1 to 4 carbon atoms includes a methoxy group, ethoxy group, propoxy group, isopropoxy group, butoxy group, isobutoxy group, 1-methylpropoxy group, t-butoxy group, or the like. From the viewpoint of efficiency of introduction of the compound to be administered, $X^3$ is preferably hydroxyl group, amino group, t-butoxy group, or benzyloxy group, further preferably hydroxyl group and amino group, and most preferably amino group.

In the polymer compound having a group represented by the general formula (1) at the side chain, when there are multiple groups represented by the general formula (1), each of $X^1$, $X^2$, $X^3$ and "a" of group represented by the general formula (1) may be the same or different.

(Group of general formula (2))

In the general formula (2), $X^4$ represents a residue of a neutral amino acid or $\omega$-aminoalkanoic acid in which an end amino group and an end carboxyl group are removed, and "b" is an integer of 0 to 50. The same neutral amino acids as those used for $X^1$ in the above general formula (1) can be used as neutral amino acids. From the viewpoint of exhibiting the effect of the present invention, the number of "a" is preferably 0 to 30, more preferably 0 to 20, most preferably 0 to 10. In an embodiment, b is 0, and in an embodiment, b is 4.

In the general formula (2), $X^5$ represents a residue of a cell-penetrating peptide in which an end amino group and an end carboxyl group are removed.

The same cell-penetrating peptide residues as those used for $X^2$ in the above general formula (1) can be used as the cell-penetrating peptide residue of polymer compound of the present invention. Further, the basic amino acid can be either L-amino acid or D-amino acid, but preferably D-amino acid. Since D-amino acids are not usually present in the body, they are less likely to be degraded, and there is a possibility that the effect of the composition of the present invention is maintained.

The same basic amino acids as those used for $X^1$ in the above general formula (1) can be used as basic amino acids.

The number of amino acids constituting cell-penetrating peptide residues is preferably 5 to 30, more preferably 6 to 20, and most preferably 7 to 15, since the introduction efficiency of the compound to be administered increases.

Specific cell-penetrating peptides include cell-penetrating peptides similar to those used for $X^2$ in the above general formula (1). When arginine oligomers are used as cell-penetrating peptides, the number of repeats of arginine is preferably 7 to 20, more preferably 7 to 15, and most preferably 7 to 10, from the viewpoint of exhibiting the effect of the present invention. In an embodiment, the number of arginine repeats is 8.

In the general formula (2), $X^6$ represents a hydrogen atom, an alkyl group having 1 to 6 carbon atoms, a benzyl group, an acyl group having 1 to 6 carbon atoms, an arylsulfonyl group or an oxycarbonyl group. Alkyl groups with 1 to 6 carbon atoms include a methyl group, ethyl group, propyl group, isopropyl group, butyl group, isobutyl group, secondary butyl group, t-butyl group, pentyl group, isopentyl group, secondary pentyl group, t-pentyl group, hexyl group, secondary hexyl group, or the like. Acyl groups having 1 to 6 carbons include a formyl group, acetyl group, propynoyl group, butynoyl group, pentynoyl group, hexynoyl group, or the like. Arylsulfonyl groups include p-toluenesulfonyl group, 2-nitrobenzenesulfonyl group, trifluoroacetyl group, or the like. Oxycarbonyl groups include, for example, a t-butoxycarbonyl group, benzyloxycarbonyl group, 9-fluorenylmethyloxycarbonyl group, 2,2,2-trichloroethoxycarbonyl group, or allyloxycarbonyl group, or the like. From the viewpoint of efficiency of introduction of the compound to be administered, $X^6$ is preferably acetyl group, hydrogen atom, methyl group, or trifluoroacetyl group, more preferably acetyl group or hydrogen atom, most preferably acetyl group.

In the polymer compound having a group represented by the general formula (2) at the side chain, when there are multiple groups represented by the general formula (2), each of $X^4$, $X^5$, $X^6$ and "b" of group represented by the general formula (2) may be the same or different.

Main Chain Polymer of Polymer Compound

The part of the main chain of the polymer compound is referred to as a main chain polymer. The main chain polymer of the graft-type polymer is not particularly limited, but it is preferably a hydrophilic polymer because of its excellent affinity with water-soluble high molecular substances such as cells and proteins. Herein, the hydrophilic polymer means a water-soluble polymer or a polymer that swells in water. In the present invention, the water-soluble polymer is a polymer that is uniformly soluble in water at 25° C. under normal pressure in an amount of 0.1% by weight or more.

The hydrophilic polymers include, for example, polysaccharides such as guar gum, agarose, mannan, glucomannan, polydextrose, lignin, chitin, chitosan, carageenan, pullulan, chondroitin sulfate, cellulose, hemicellulose, methylcellulose, ethylcellulose, hydroxyethylcellulose, hydroxypropylcellulose, starch, cationic starch, and dextrin, or modified polysaccharides; water-soluble proteins or water-soluble polypeptides such as albumin, casein, gelatin, polyglutamic acid, and polylysine; vinyl-based hydrophilic polymer such as poly(meth)acrylic acid, poly(hydroxyethyl acrylate), poly (meth)acrylamide, polyN-vinylacetamide, polyvinylpyrrolidone, polyvinyl alcohol, poly(2-aminoethyl(meth)acrylate), (meth)acrylic acid-acrylamide copolymer, (meth)acrylic acid-N-isopropylacrylamide copolymer, (meth)acrylic acid-N-vinylacetamide copolymer, (meth)acrylic acid-maleic acid copolymer, (meth)acrylic acid-fumaric acid copolymer, ethylene-maleic acid copolymer, isobutylene-maleic acid copolymer, styrene-maleic acid copolymer, alkyl vinyl ether-maleic acid copolymer, alkyl vinyl ether-fumaric acid copolymer; and water-soluble polyurethane. From the viewpoint of exhibiting the effect of the present invention remarkably, the vinyl-based hydrophilic polymer is preferable.

Since grafting of cell-penetrating peptide residues into the main chain polymer is facilitated, when the polymer compound of the present invention is a polymer compound having a group represented by the general formula (1) at the side chain, a polymer having a carboxyl group is preferable as the main chain polymer, and a hydrophilic polymer having a carboxyl group is more preferable, and a copolymer of monomers having a carboxyl group and monomers without a carboxyl group are further preferable, and a (meth) acrylic acid-N-vinylacetamide copolymer is most preferable.

In the polymer compound having the group represented by the general formula (2) at the side chain, grafting of cell-penetrating peptide residues into the main chain polymer is facilitated, and thus a polymer having an amino group is preferable, a hydrophilic polymer having an amino group is more preferable, and chitosan is most preferable. The wording "having an amino group or a carboxyl group" means that the main chain polymer before having the group represented by the general formula (1) or (2) at the side chain has an amino group or a carboxyl group.

When the main chain polymer has the carboxyl group, the ratio of the number of monomer units having the carboxyl group with respect to the number of monomer units constituting the main chain polymer is preferably 5 to 80%, and more preferably 10 to 60%, from the viewpoint of obtaining a preferable polymer compound in the present invention.

When the main chain polymer has the amino group, the ratio of the number of monomer units having the amino group with respect to the number of monomer units constituting the main chain polymer is preferably 5 to 100%, and more preferably 10 to 100%, from the viewpoint of obtaining a preferable polymer compound in the present invention. The ratio of units having amino groups or carboxyl groups described above preferably applies to the main chain polymer before having the group represented by the general formula (1) or (2) at the side chain.

The polymer compound is characterized in that it has the group represented by the general formula (1) or the general formula (2) at the side chain. If the ratio of the groups represented by the general formula (1) or (2) in the polymer compound of the present invention is too low or too high, the introduction efficiency of the compound to be administered will be low. From the viewpoint of preventing this point, the number of groups represented by the general formula (1) or (2) in the polymer compound of the present invention with respect to the number of monomer units (monosaccharide units in the case of polysaccharides or modified polysaccharides, amino acid units in the case of water soluble proteins or water soluble polypeptides) constituting the main chain polymer is preferably 0.001 to 0.9, more preferably 0.005 to 0.8, and most preferably 0.01 to 0.7.

Taking advantage of the characteristics of the polymeric compound of the present invention, it is desirable to facilitate the accidental and continuous uptake of the administered compound into cells, as described below. In addition, when the polymer compound of the present invention is too large, the introduction efficiency of the compound to be administered decreases, and thus it is desirable to prevent from decreasing. From the above viewpoints, the weight average molecular weight of the polymer compound in the present invention is preferably 20,000 to 50,000,000, more preferably 100,000 to 30,000,000, further preferably 200,000 to 10,000,000, and most preferably 250,000 to 1,000,000. The above lower limits and upper limits can be appropriately combined.

In the present specification, the weight average molecular weight is the weight average molecular weight when GPC analysis is performed using an aqueous solvent. If the main chain polymer is the polysaccharide or modified polysaccharide, or the water-soluble protein, it is the weight average molecular weight converted to pullulan. If the main chain polymer is the vinyl hydrophilic polymer, it is the weight average molecular weight converted to polyethylene glycol (PEG) or polyethylene oxide (PEO).

The molecular weight in GPC measurement, for example, can be measured by the following apparatus and columns.

Apparatus; EXTREMA (JASCO Corporation)

Columns: TSKgel G4000 PWXLx2 or TSKgel G6000 PWXL-CP+G3000 PWXL-CP (Tosoh Corporation)

The production method of the polymer compound is not particularly limited. It may be produced by polymerizing a polymerizable monomer having a group represented by general formula (1) or general formula (2), or by introducing a group represented by general formula (1) or general formula (2) into the main chain polymer. From the viewpoint of ease of production, it is preferable to prepare the polymer by introducing the group represented by general formula (1) or general formula (2) into the main chain polymer. When the main chain polymer is a hydrophilic polymer having a carboxyl group, it can be obtained by peptide-reacting the carboxyl group with an amino group of a peptide compound represented by the following general formula (1b). Regarding the reaction of the carboxyl group with the amino group, known methods can be used. For example, it includes a method wherein the carboxylic group is succimidated by N-hydroxy succinimide, and then the amino group is reacted therewith.

When the main chain polymer is a hydrophilic polymer having an amino group, it can be obtained by peptide-reacting the amino group with the carboxyl group of a peptide compound represented by the following general formula (2b). According to this method, the groups represented by the general formula (1) or (2) can be most easily introduced into the side chain of the main chain polymer via an amide bond. However, the method of immobilization of the group represented by the general formula (1) or (2) is not limited to this method, but any commonly known chemical reaction can be used to immobilize the groups.

[Chem. 5]

(1b)

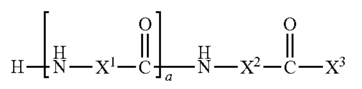

(In the above formula, $X^1$, $X^2$, $X^3$ and a are synonymous with general formula (1).)

[Chem. 6]

(2b)

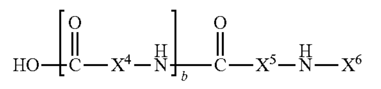

(In the above formula, $X^4$, $X^5$, $X^6$ and a are synonymous with general formula (2).)

The mechanism of cellular uptake of cell-penetrating peptides is generally that cell-penetrating peptides induce macropinocytosis of cells. When compounds are present in the surrounding area of cells, it is considered that these compounds are taken up together with the cell-penetrating peptides. In the polymer compound of the present invention, macropinocytosis is induced at multiple locations in cells by cell-penetrating peptide residues. However, the polymer compound of the present invention is large molecules, and therefore it is difficult for cells to take up one molecule of the polymer compound of the present invention through multiple locations in the cell. Therefore, the compound to be administered in the present invention is taken up accidentally and continuously by the cells in which macropinocytosis is induced, through the composition of the present invention. In addition, in the composition of the present invention, the combination of the polymer compound and the compound to be administered allows the interaction between the polymer compound and the compound to be administered. Therefore, even high molecular weight compounds such as antibody drugs are more efficiently introduced into cells.

An amount of the polymer compound in the composition of the present invention is not particularly limited. From the viewpoint of exhibiting the effect of the present invention, however, it is preferably 0.00001 to 20% by weight, more preferably 0.0001 to 15% by weight, and even more preferably 0.0001 to 10% by weight, and most preferably 0.0001 to 5% by weight.

Pharmaceutical Composition

The composition of the present invention is not limited, but can be used as pharmaceutical composition. The active ingredient of the pharmaceutical composition is the compound to be administered. The amount of the compound to be administered in the pharmaceutical composition depends on the compound to be administered, to be used. However, in the case of an adult, the pharmaceutical composition should contain 10 mg to 4 g per day, preferably 20 mg to 2 g per day. Specifically, the content of the active ingredient in the pharmaceutical composition is preferably to 40% by weight, more preferably 0.0001 to 30% by weight, and most preferably 0.0001 to 20% by weight, from the viewpoint of exhibiting the effect of the present invention.

In the composition of the present invention, it is preferred that the weight ratio of (A) polymer compound and (B) dosage compound be contained in the range of (A):(B)=0.1:1 to 20:1. The range of 0.1:1 to 10:1 is more preferable, the range of 0.1:15:1 is further more preferable, the range of 0.5:1 to 3:1 is even more preferable, the range of 0.5:1 to 2:1 is most preferable. According to the above range, the effect of the present invention can be remarkably exhibited.

The formulation of the pharmaceutical composition of the present invention is not particularly limited. For example, there may be mentioned oral agents, such as powders, subtle granules, granules, tablets, capsules, suspensions, emulsions, sylups, extracts, or balls; or parentarnal agents, such as injections, liquid for external use, ointments, suppositories, creams for local administration, or eye-drops. In the oral agents, it can be administered as a food and drink, such as a functional food, a healthy food (including drink), or an animal food stuff.

The pharmaceutical composition can be prepared in accordance with conventional methods, using fillers, such as gelatin, alginate sodium, starch, cornstarch, saccharose, lactose, glucose, mannitol, carboxymethyl-cellulose, dextrin, polyvinyl pyrrolidone, clystalline cellulose, soy lecithin, sucrose, fatty acid ester, talc, magnesium stearate, polyethylene glycol, magnesium silicate, silicic anhydride, or synthetic aluminum silicate; binders, disintegrators, detergents, lubricants, flow accelerator, diluents, preservatives, colorants, flavors, correctives, stabilizers, humectants, antiseptics, antioxidant, or the like, in addition to the polymer compound and the compound to be administered.

A dose of the pharmaceutical composition may be appropriately determined in accordance with, for example, age, sex, body weight, or degree of symptom of each patient, the type of each active ingredient, type of each disease, route of administration, or the like, and the determined dosage can be administered orally or parenterally. The pharmaceutical composition can be administered, in an effective amount, together with a pharmaceutically or veterinarily acceptable carrier or diluent, to a subject (for example, an animal, preferably a mammal, particularly a human).

The composition of the present invention can be used, for contacting cells after mixing the polymer compound and the compound to be administered, but is not limited thereto. For example, when the polymer compound and the compound to be administered are contained in the composition in powder form, the polymer compound and the compound to be administered can be brought into contact with the cells after being mixed as a solution or suspension in which the polymer compound and the compound to be administered can interact with each other. The interaction between the polymer compound and the compound to be administered allows the compound to be administered to be efficiently taken up by the cells.

The composition of the present invention can be used on mucous membranes to introduce the compounds to be administered into cells in various mucous membranes.

The mucous membranes include the nasal mucosa, oral mucosa, vaginal mucosa, rectal mucosa, ocular mucosa, gastric mucosa, intestinal mucosa or the like. When the composition is used on mucous membranes, it is preferable to administer it by liquid, gel, or spray. A contact time between the composition and the cells (mucosa) is not limited, but is preferably 30 minutes to 24 hours.

The cells to which the composition of the present invention is administered may be animal, plant, or bacterial cells. When the composition is applied to cells in vitro, it is possible to introduce the compound to be administered into cells dispersed in culture medium (also called liquid medium), cells adhering to solid medium, or cells in living tissues. Cells can be roughly classified into adhesive cells, which form tissue cells, nerve cells, or the like, and floating cells, such as hematopoietic cells. The composition of the present invention can introduce the compound to be administered into not only adherent cells but also floating cells with high efficiency.

EXAMPLES

The present invention will now be further illustrated by, but is by no means limited to, the following Examples.

Polymer compounds for use in the compositions of the present invention were prepared in the following manufacturing examples 1 to 5.

Manufacturing Example 1

In this manufacturing example, an acrylic acid-N-vinylacetamide copolymer was used as a main chain polymer, and a polymer compound having D-octaarginine as a side chain was prepared.

A copolymer (NVA-AANa polymer) was synthesized according to the usual method, using g of sodium acrylate and 70 g of N-vinylacetamide as raw materials, referring to Example 14 in JP08-081428.

Then, a 20-mm-diameter column tube was packed with a cation exchange resin (IR120B, Organo), and 130 g of aqueous solution of 5.0 weight % NVA-AANa polymer was passed through at 2.6 mL/min to obtain an aqueous solution of NVA-AA polymer. The resulting aqueous solution of NVA-AA polymer was lyophilized to obtain 5.7 g of NVA-AA polymer.

In a 300-mL four-necked flask, 5.0 g of NVA-AA polymer was dissolved in 142 g of N,N'-dimethylformamide (DMF), and the resulting solution was cooled at 10° C. or less. To this solution, 58 g (0.2 g/mL) of a DMF solution of N-hydroxy succinimide and 66 g (0.4 g/mL) of a DMF solution of N,N'-dicyclohexylcarbodiimide were added. After stirring for 1 hour under an ice bath, the temperature was raised to room temperature and stirred for 24 hours. The reaction solution was filtered by suction, and the filtrate was re-precipitated using 2 L of acetonitrile. Then, the precipitate was washed with 2 L of acetone and the solid was collected by suction filtration. The solid was dried under reduced pressure to give 5.4 g of a succinimide-esterified NVA-AA polymer (NVA-AA OSu).

52 mg of NVA-AA OSu was dissolved in 2.4 mL of DMF. To this solution, 0.50 mL of DMF solution of a basic peptide (NH2-R8/D, trifluoroacetate, Sigma-Aldrich) consisting of 8 D-arginine (in the general formula (1b), a is 0, $X^2$ is the residue in which the terminal amino group and the terminal carboxyl group were removed from D-octaarginine, $X^3$ is the amino group) (400 mg/mL), and 0.01 mL of triethylamine (TCI) were added, and the reaction was performed by stirring at 50° C. for 24 hours. Then, the reaction solution was transferred to a cellulose dialysis tube (seamless cellulose tube, made by Spectrum, MWCO: 3.5 kDa), the two ends of the tube were tied, and the tube was dialyzed with ultrapure water for 3 days. Then, the contents in the tube were lyophilized to obtain 110 mg of the polymer compound of manufacturing Example 1 (hereinafter referred to as VP-$R_8$/D) (general formula (3)). The polymer compound of manufacturing Example 1 is a compound wherein a is 0, $X^2$ is a residue in which the terminal amino group and the terminal carboxyl group were removed from D-octaarginine, and $X^3$ is an amino group, in the general formula (1). According to GPC analysis, the weight-average molecular weight of VP-R8/D is 350000 (PEG/PEO conversion), and NMR integrated values indicate that it has the following structure. In the formula, Arg represents an arginine residue, and 1H-NMR analysis showed that the ratio of x:y:z=70:21:9 (molar ratio).

[Chem. 7]

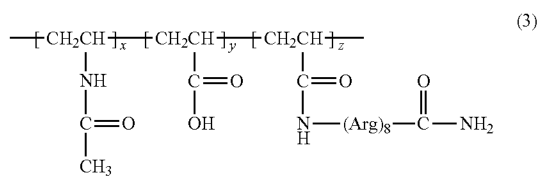

(3)

Molecular weights in GPC analysis were measured by the following apparatus and columns under the following conditions.

Apparatus EXTREMA (JASCO Corporation.)
Columns TSKgel G6000 PWXL-CP+G3000 PWXL-CP (Tosoh Corporation)
Eluent 0.1M phosphate buffer (pH=2.7)
Flow rate 0.6 mL/min
Measurement temperature 60° C.
Detection RI
Analysis time: 90 min.
Sample concentration 3 mg/mL
Sample injection volume 50 μL

Manufacturing Example 2

The same procedure (same amounts of agents) described in Manufacturing Example 1 was repeated, except that L-octaarginine was used instead of $X^2$ in Manufacturing Example 1, to obtain 110 mg of the polymer compound of Manufacturing Example 2 (hereinafter referred to as VP-$R_8$/

L). GPC analysis (under the same conditions as in Manufacturing Example 1) revealed that the weight-average molecular weight of VP-$R_8$/L is 370,000 (PEG/PEO conversion), and the NMR integrated values indicate that it has the structure of Formula (3). The 1H-NMR analysis showed that the ratio of x:y:z=70:19:11 (molar ratio).

Manufacturing Example 3

To 0.8 mL dimethyl sulfoxide (DMSO), 20 mg of hyaluronic acid (derived from chicken crown, manufactured by Tokyo Chemical Industry Co., Ltd) was dissolved.

To this solution, 18 mg of N-hydroxy succinic imide dissolved in 0.1 mL of DMSO was added, and then 33 mg of N,N'-dicyclohexylcarbodiimide dissolved in 0.1 mL of DMSO was added and the whole was reacted by stirring at 25° C. for 24 hours. The precipitated solid was filtered and mL of DMSO was added to obtain a DMSO solution of succinimide-esterified hyaluronic acid. To this solution, 0.40 mL of a DMSO solution of a basic peptide consisting of 4 glycine and 8 L-arginine ($NH_2$-$G_4R_8$/L, trifluoroacetate salt, Sigma-Aldrich, terminal carboxyl group is amidated) (400 mg/mL), and 0.02 mL of triethylamine were added, and the whole was reacted by stirring at 25% for 24 hours. Then, the reaction solution was transferred to a cellulose dialysis tube (seamless cellulose tube, made by Spectrum, MWCO: 3.5 kDa), the two ends of the tube were tied, and the tube was dialyzed with ultrapure water for 7 days. Then, the contents in the tube were lyophilized to obtain 100 mg of the polymer compound of Manufacturing Example 3 (hereinafter referred to as HA-$G_4R_8$/L) (general formula (4)). The polymer compound in manufacturing Example 3 is a compound wherein a is 4, $X^1$ is a residue in which the terminal amino group and the terminal carboxyl group were removed from L-glycine, $X^2$ is a residue in which the terminal amino group and the terminal carboxyl group were removed from L-octaarginine, and $X^3$ is an amino group, in the general formula (1) (general formula (4)), and d/(c+d) is 1.0 (1H-NMR integral value).

According to GPC analysis, the weight-average molecular weight of HA-$G_4R_8$/L is 44,000 (pullulan conversion).

[Chem. 8]

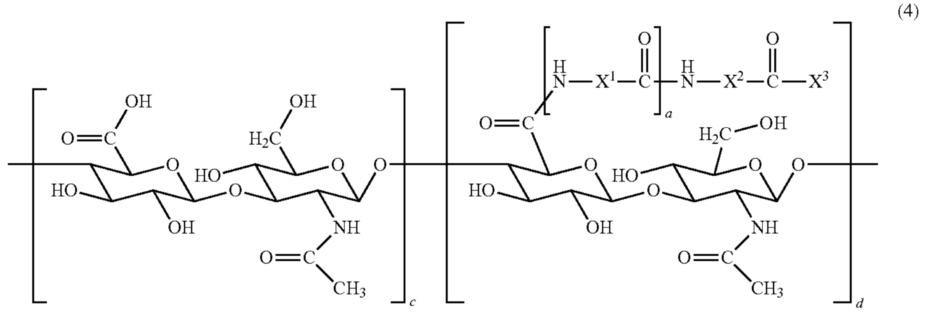

(4)

Molecular weights in GPC analysis were measured by the following apparatus and columns under the following conditions.

Apparatus EXTREMA (JASCO Corporation.)
Columns TSKgel G4000 PWXL×2 (Tosoh Corporation)
Eluent 0.5M acetic acid+0.1M sodium nitrate aqueous solution
Flow rate 1 mL/min
Measurement temperature 40° C.
Detection RI
Analysis time: 45 min.
Sample concentration 3 mg/mL
Sample injection volume 50 μL Manufacturing Example 4

D-octaarginine (hereinafter referred to as $NH_2$-$R_8$/D, Sigma-Aldrich) was used as Manufacturing Example 4.

Manufacturing Example 5

Sodium salcaprozate (hereinafter referred to as SNAC, Synchem) was used as Manufacturing Example 5.

Model Drugs

FITC-INS: FITC-labeled insulin (peptide-protein drug, molecular weight 5,800, Sigma-Aldrich, final concentration 5 μg/mL)
FITC-CTB: FITC-labeled choleratoxin B subunit (protein, molecular weight 11,000, Sigma-Aldrich, final concentration 5 μg/mL)
FITC-OVA: FITC-labeled ovalbumin (protein, molecular weight 45,000, Thermo Fisher Scientific, final concentration 5 μg/mL)
FITC-IgG: FITC-labeled human immunoglobulin G (human antibody, molecular weight 150,000, Sigma-Aldrich, final concentration 5 μg/mL)
FITC-Tf: FITC-labeled transferrin (protein, molecular weight 77,000, Thermo Fisher Scientific, final concentration 5 μg/mL)
FITC-IgM: FITC-labeled human immunoglobulin M (human antibody, molecular weight 900,000, synthesized in-house, final concentration 5 μg/mL)

Evaluation of Cellular Uptake

Cellular uptake evaluation of the model drugs described above was conducted using Examples 1 to 3 (polymeric compounds of Manufacturing Examples 1 to 3) or Comparative Examples 1 to 2 (compounds of Manufacturing Examples 4 and 5). A suspension of Ham's F-12 medium (manufactured by Fujifilm Wako Chemical Corporation) containing Chinese hamster ovary cells (CHO cells, $2\times10^5$ cells/mL) was prepared and seeded at 500μL/well to each well of a 24-well plate. The cells were incubated in a $CO_2$ gas incubator (37° C., 5% $CO_2$) for 24 hours.

Then, the compositions of the Examples and Comparative Examples (Table 1-6) were prepared by mixing 250 μL/well of Ham's F-12 medium containing the above model drugs and 250 μL/well of Ham's F-12 medium containing the manufacturing examples. The final concentrations of the examples in the Ham's F-12 medium were determined as follows, by individually evaluating the concentrations that do not exhibit any cytotoxity to CHO cells.

Manufacturing Example 1: Final concentration 5 μg/mL

Manufacturing Example 2: Final concentration 5 μg/mL

Manufacturing Example 3: Final concentration 101 μg/mL

Manufacturing Example 4: Final concentration 1701 μg/mL

Manufacturing Example 5: Final concentration 30001 μg/mL

Then, the supernatant was removed from each well of the pre-cultured 24-well plate using an aspirator and the cells were washed twice with 500 μL/well of phosphate-buffered saline. Then, the aforementioned compositions were gently added to the wells and incubated in a carbon dioxide incubator for 2 hours. The number of experiments was n=3.

After 2 hours, the supernatants of medium were removed, and the cells were washed twice with 500 μL/well of phosphate-buffered saline. Then, 100 μL/well of trypsin-EDTA solution (0.25% trypsin, 1 mmol/L EDTA solution, Life Technologies) was added, and cultured CHO cells were detached from 24-well plates.

Then, 400 μL/well of trypan blue solution (Fujifilm Wako Chemical Corporation) was added to suspend the cells, and the cells were collected in microtubes. The collected cell suspensions were passed through a cell strainer, and the mean fluorescence intensity (MFI) was measured by flow cytometry. The cells without the polymeric compound (only the model drug was added) were used as controls.

The FITC-labeled model drug adsorbed on the outside of the cells was quenched by trypan blue and does not emit fluorescence. While only the model drug introduced into the cells emits fluorescence. MFI represents the arithmetic average of the fluorescence intensity per cell, and a larger value of MFI indicates a more efficient intracellular uptake of the model drug.

The results of the cellular uptake evaluation of FITC-INS are shown in Table 1 and FIG. 1. The results of the cellular uptake evaluation of FITC-CTB are shown in Table 2 and FIG. 2. The results of cellular uptake of FITC-OVA are shown in Table 3 and FIG. 3. The results of the cellular uptake evaluation of FITC-IgG are shown in Table 4 and FIG. 4. The results of the cellular uptake evaluation of FITC-Tf are shown in Table 5 and FIG. 5. The results of the cellular uptake evaluation of FITC-IgM are shown in Table 6 and FIG. 6.

The cellular uptake of the model drugs in Examples 1 to 3 was better than that in Comparative Examples 1 and 2, and the trend of the results was more remarkable in the range of high molecular weight of the model drug. From these results, it was found that the compositions of Examples 1 to 3 can be taken up into the cells well even in combination with high molecular weight compounds such as antibodies. In addition, the cellular uptake of the model drug was better in Example 1, which contains a high molecular weight compound of the D-amino acid, than in Example 2, which contains a high molecular weight compound of the L-amino acid.

The cellular uptake of the model drug was better in Examples 1 and 2 than in Example 3, which contained hyaluronic acid as the polymer compound. Further, it was found that the Examples showed better cellular uptake of the model drug than the Comparative Examples at lower final concentrations.

TABLE 1

| Model drug: FITC-INS (Molecular weight 5,800) | | |
|---|---|---|
| | Polymer compound (Manufacturing example) | MFI ± S.D. |
| Control | Not used | 6.2 ± 0.4 |
| Comparative Example 1 | $NH_2$—$R_8$/D (Manufacturing example 4) | 27.4 ± 1.2 |
| Comparative Example 2 | SNAC (Manufacturing example 5) | 19.7 ± 0.2 |
| Example 1 | VP—$R_8$/D (Manufacturing example 1) | 472.2 ± 20.4 |
| Example 2 | VP—$R_8$/L (Manufacturing example 2) | 208.3 ± 29.2 |
| Example 3 | $HAG_4R_8$/L (Manufacturing example 3) | 112.5 ± 16.6 |

TABLE 2

| Model drug: FITC-CTB (Molecular weight 11,000) | | |
|---|---|---|
| | Polymer compound (Manufacturing example) | MFI ± S.D. |
| Control | Not used | 3.4 ± 0.0 |
| Comparative Example 1 | $NH_2$—$R_8$/D (Manufacturing example 4) | 32.7 ± 4.7 |
| Comparative Example 2 | SNAC (Manufacturing example 5) | 3.7 ± 0.1 |
| Example 1 | VP—$R_8$/D (Manufacturing example 1) | 241.4 ± 52.8 |
| Example 2 | VP—$R_8$/L (Manufacturing example 2) | 163.7 ± 3.6 |
| Example 3 | $HAG_4R_8$/L (Manufacturing example 3) | 176.6 ± 9.0 |

TABLE 3

| Model drug: FITC-OVA (Molecular weight 45,000) | | |
|---|---|---|
| | Polymer compound (Manufacturing example) | MFI ± S.D. |
| Control | Not used | 3.4 ± 0.1 |
| Comparative Example 1 | $NH_2$—$R_8$/D (Manufacturing example 4) | 14.3 ± 2.5 |
| Comparative Example 2 | SNAC (Manufacturing example 5) | 3.6 ± 0.4 |
| Example 1 | VP—$R_8$/D (Manufacturing example 1) | 946.6 ± 122.3 |
| Example 2 | VP—$R_8$/L (Manufacturing example 2) | 594.5 ± 9.2 |
| Example 3 | $HAG_4R_8$/L (Manufacturing example 3) | 218.0 ± 29.9 |

TABLE 4

| Model drug: FITC-IgG (Molecular weight 150,000) | | |
|---|---|---|
| | Polymer compound (Manufacturing example) | MFI ± S.D. |
| Control | Not used | 3.2 ± 0.1 |
| Comparative Example 1 | $NH_2$—$R_8$/D (Manufacturing example 4) | 3.3 ± 0.0 |
| Comparative Example 2 | SNAC (Manufacturing example 5) | 3.2 ± 0.1 |

TABLE 4-continued

| Model drug: FITC-IgG (Molecular weight 150,000) | | |
|---|---|---|
| | Polymer compound (Manufacturing example) | MFI ± S.D. |
| Example 1 | VP—$R_8$/D (Manufacturing example 1) | 122.1 ± 15.5 |
| Example 2 | VP—$R_8$/L (Manufacturing example 2) | 76.2 ± 35.3 |
| Example 3 | $HAG_4R_8$/L (Manufacturing example 3) | 17.2 ± 4.2 |

TABLE 5

| Model drug: FITC-Tf (Molecular weight 77,000) | | |
|---|---|---|
| | Polymer compound (Manufacturing example) | MFI ± S.D. |
| Control | Not used | 5.2 ± 0.3 |
| Comparative Example 1 | $NH_2$—$R_8$/D (Manufacturing example 4) | 9.8 ± 0.8 |
| Comparative Example 2 | SNAC (Manufacturing example 5) | 6.7 ± 0.2 |
| Example 1 | VP—$R_8$/D (Manufacturing example 1) | 88.2 ± 2.9 |
| Example 2 | VP—$R_8$/L (Manufacturing example 2) | 43.2 ± 7.7 |
| Example 3 | $HAG_4R_8$/L (Manufacturing example 3) | 20.7 ± 0.6 |

TABLE 6

| Model drug: FITC-IgM (Molecular weight 900,000) | | |
|---|---|---|
| | Polymer compound (Manufacturing example) | MFI ± S.D. |
| Control | Not used | 2.9 ± 0.0 |
| Comparative Example 1 | $NH_2$—$R_8$/D (Manufacturing example 4) | 5.9 ± 0.4 |
| Comparative Example 2 | SNAC (Manufacturing example 5) | 3.1 ± 0.2 |
| Example 1 | VP—$R_8$/D (Manufacturing example 1) | 447.4 ± 3.1 |
| Example 2 | VP—$R_8$/L (Manufacturing example 2) | 277.2 ± 8.6 |
| Example 3 | $HAG_4R_8$/L (Manufacturing example 3) | 121.7 ± 12.2 |

INDUSTRIAL APPLICABILITY

The compositions of the present invention can be used for intracellular administration of high molecular weight compounds such as antibody drugs.

The invention claimed is:

1. A composition comprising a polymer compound having a group represented by the following general formula (1) or the following general formula (2) at a side chain, and a compound to be administered with a molecular weight of 85,000 to 1,200,000:

(1)

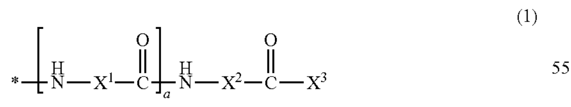

wherein $X^1$ is a residue of neutral amino acid or ω-aminoalkanoic acid in which an end amino group and an end carboxyl group are removed, $X^2$ is a residue of cell-penetrating peptide in which an end amino group and an end carboxyl group are removed, $X^3$ is a hydroxyl group, an amino group, an alkoxyl group having 1 to 4 carbon atoms or a benzyloxy group, a is an integer of 0 to 50, and * denotes a bonding site, or (2)

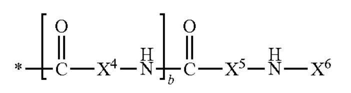

wherein $X^4$ is a residue of neutral amino acid or ω-aminoalkanoic acid in which an end amino group and an end carboxyl group are removed, $X^5$ is a residue of cell-penetrating peptide in which an end amino group and an end carboxyl group are removed, $X^6$ is a hydrogen atom, an alkyl group having 1 to 6 carbon atoms, a benzyl group, an acyl group having 1 to 6 carbon atoms, an arylsulfonyl group or an oxycarbonyl group, b is an integer of 0 to 50, and * denotes a bonding site.

2. The composition according to claim 1, wherein the molecular weight of the compound to be administered is 85,000 to 200,000.

3. The composition according to claim 1, wherein a main chain polymer of the polymer compound is a vinyl hydrophilic polymer.

4. The composition according to claim 1, wherein the compound to be administered is an antibody.

5. The composition according to claim 4, wherein the antibody is a polyclonal antibody, monoclonal antibody, chimeric antibody, humanized antibody, or human antibody, or antigen-binding fragment thereof.

6. The composition according to claim 1, for contacting cells after mixing the polymer compound and the compound to be administered.

* * * * *